(12) United States Patent
Bae et al.

(10) Patent No.: US 7,507,814 B2
(45) Date of Patent: Mar. 24, 2009

(54) PROCESS FOR PREPARATION OF IMIPENEM

(75) Inventors: Hyun Seop Bae, Seoul (KR); Tae Seop Hwang, Suwon (KR); Chan Yong Ahn, Ansan (KR); Chang Hoon Oh, Siheung (KR); Moo Sung Kim, Suwon (KR)

(73) Assignee: Choongwae Pharm. Co., Seoul (KR)

( * ) Notice: Subject to any disclaimer, the term of this patent is extended or adjusted under 35 U.S.C. 154(b) by 450 days.

(21) Appl. No.: 10/563,250

(22) PCT Filed: Dec. 9, 2004

(86) PCT No.: PCT/KR2004/003224

§ 371 (c)(1),
(2), (4) Date: Jan. 4, 2006

(87) PCT Pub. No.: WO2005/056553

PCT Pub. Date: Jun. 23, 2005

(65) Prior Publication Data

US 2006/0167243 A1    Jul. 27, 2006

(30) Foreign Application Priority Data

Dec. 9, 2003    (KR) .................... 10-2003-0088857

(51) Int. Cl.
*C07D 477/20* (2006.01)
*C07D 477/18* (2006.01)

(52) U.S. Cl. .................................... 540/350
(58) Field of Classification Search .............. 540/350
See application file for complete search history.

(56) References Cited

U.S. PATENT DOCUMENTS

| | | | | |
|---|---|---|---|---|
| 4,150,145 A | * | 4/1979 | Christensen et al. | ..... 514/210.1 |
| 4,172,144 A | * | 10/1979 | Bouffard et al. | ......... 514/210.1 |
| 4,235,920 A | * | 11/1980 | Christensen et al. | ..... 514/210.1 |
| 4,894,450 A | | 1/1990 | Grabowski et al. | |
| 2002/0095034 A1 | | 7/2002 | Zenoni et al. | |

FOREIGN PATENT DOCUMENTS

| | | | |
|---|---|---|---|
| GB | 1570988 A | * | 7/1980 |
| WO | WO 02/36594 A1 | | 5/2002 |
| WO | WO 02/094828 A1 | | 11/2002 |

* cited by examiner

*Primary Examiner*—Mark L Berch
(74) *Attorney, Agent, or Firm*—Dickstein Shapiro LLP

(57) ABSTRACT

The invention provides a novel compound of Formula II which is useful in the preparation of imipenem monohydrate of Formula I, wherein R1 is a p-nitrobenzyl or p-methoxybenzyl group; and R2 and R3 may be identical to or different from each other and are each independently a $C_{1-6}$ alkyl or aryl group, or a derivative thereof, and a process for preparing the compound of Formula II by coupling (5R,6S) p-nitrobenzyl-3-(diphenylphosphono)-6-[(1R)-1-hydroxyethyl]-1-azabicyclo[3.2.0]hept-2-ene-7-one-2-carboxylate with 2-aminoetahnethiol hydrocloride in the presence of a base, followed by a reaction with a ketone. Further, the invention provides a process for preparing the compound of Formula I by reacting a compound of Formula II with isopropylformimidate or benzylformimidate in the presence of a base, followed by hydrogenation, separation and crystallization.

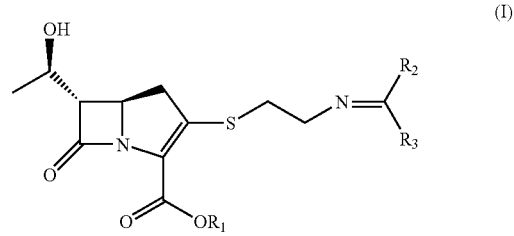

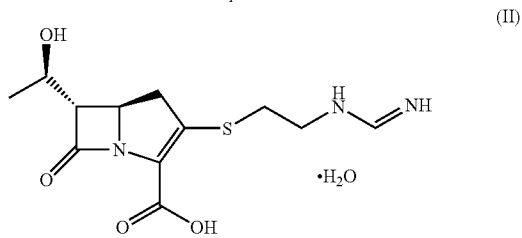

9 Claims, 6 Drawing Sheets

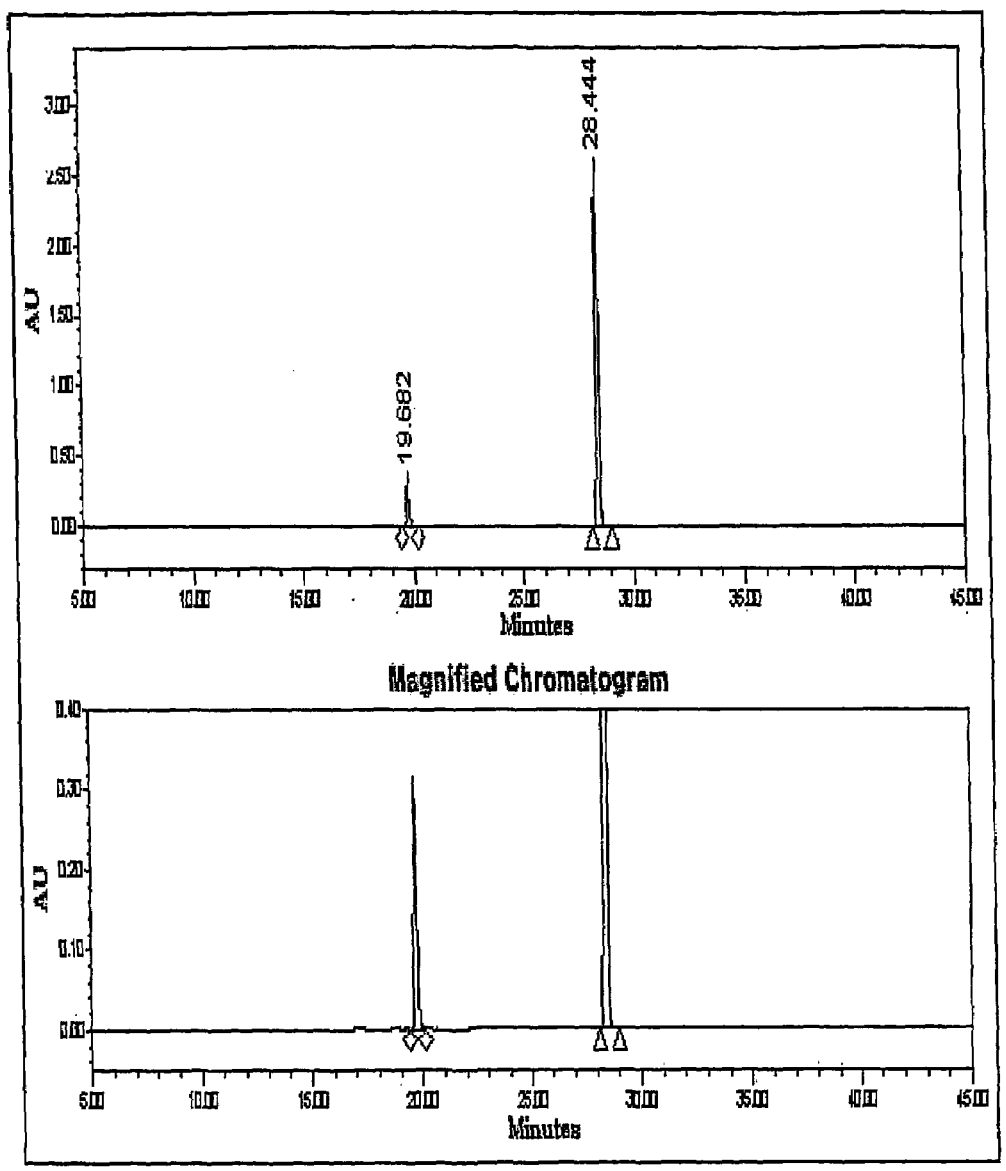

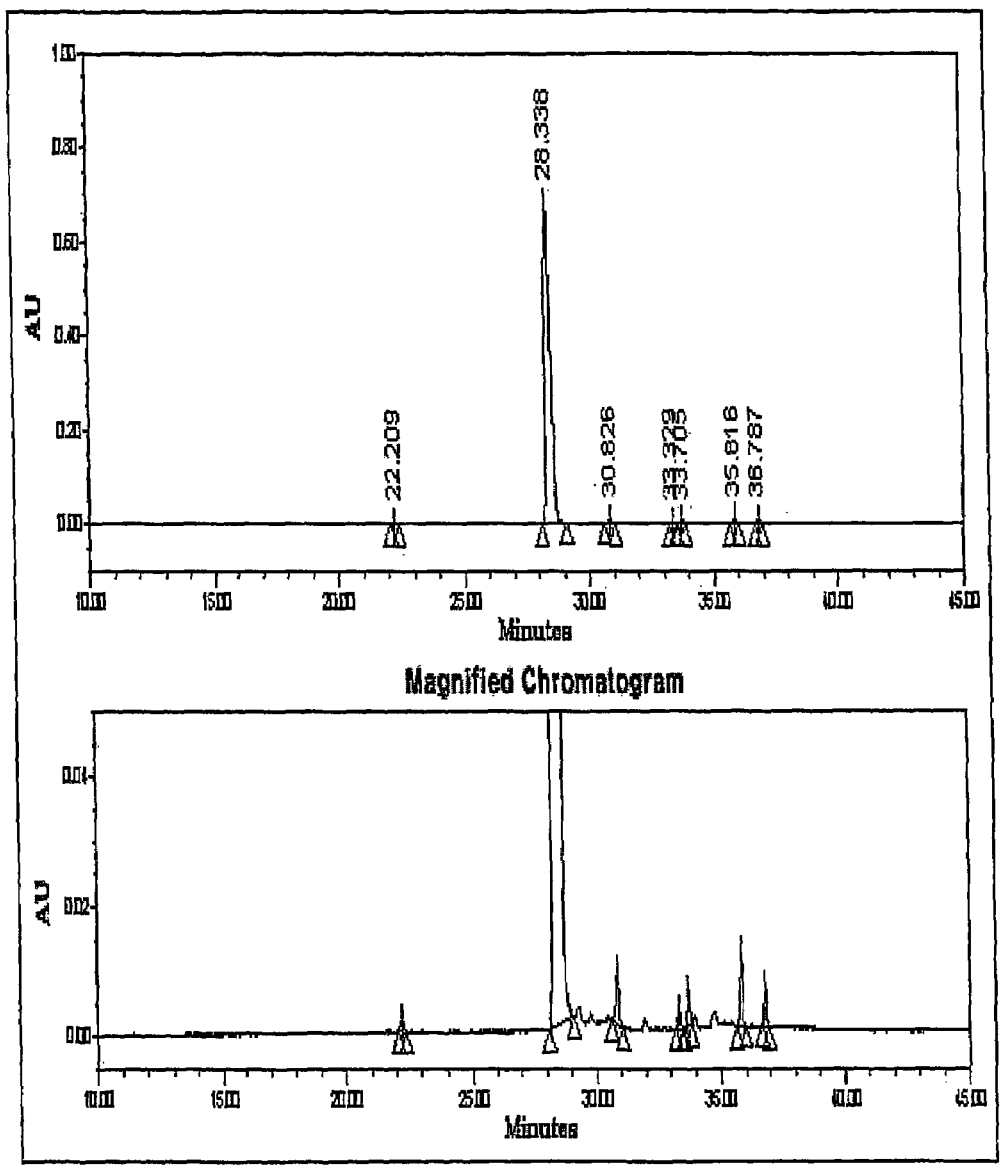

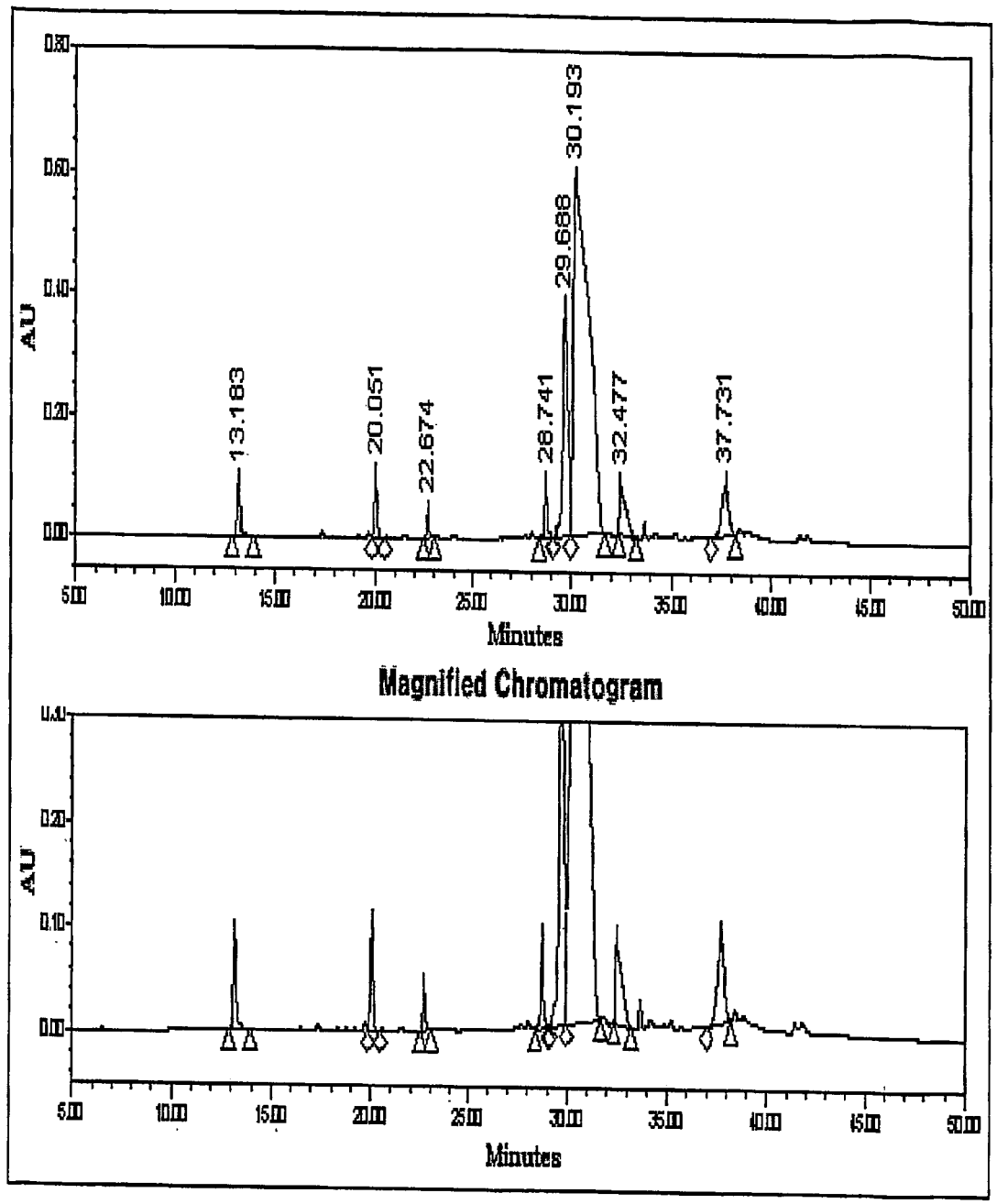

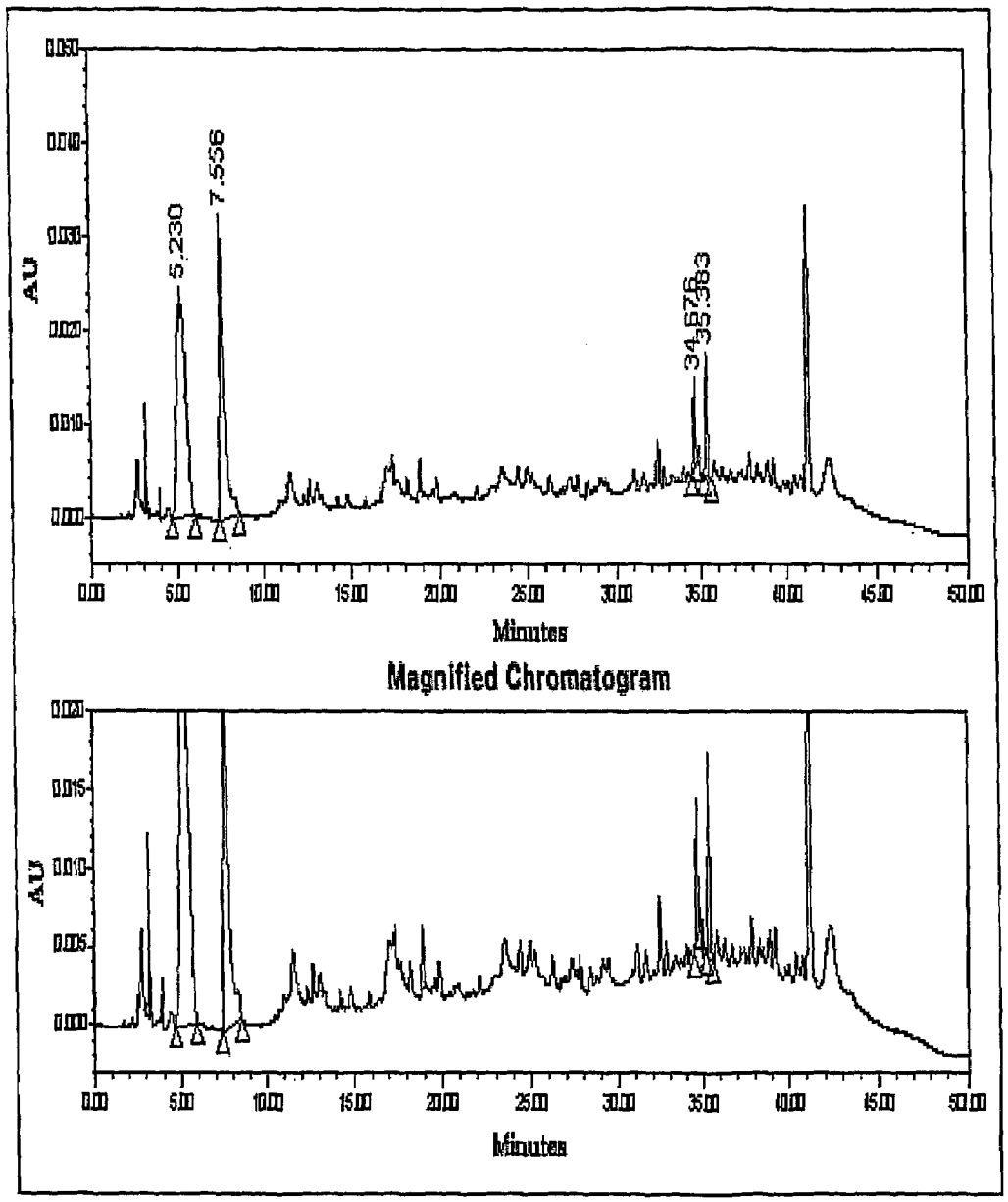

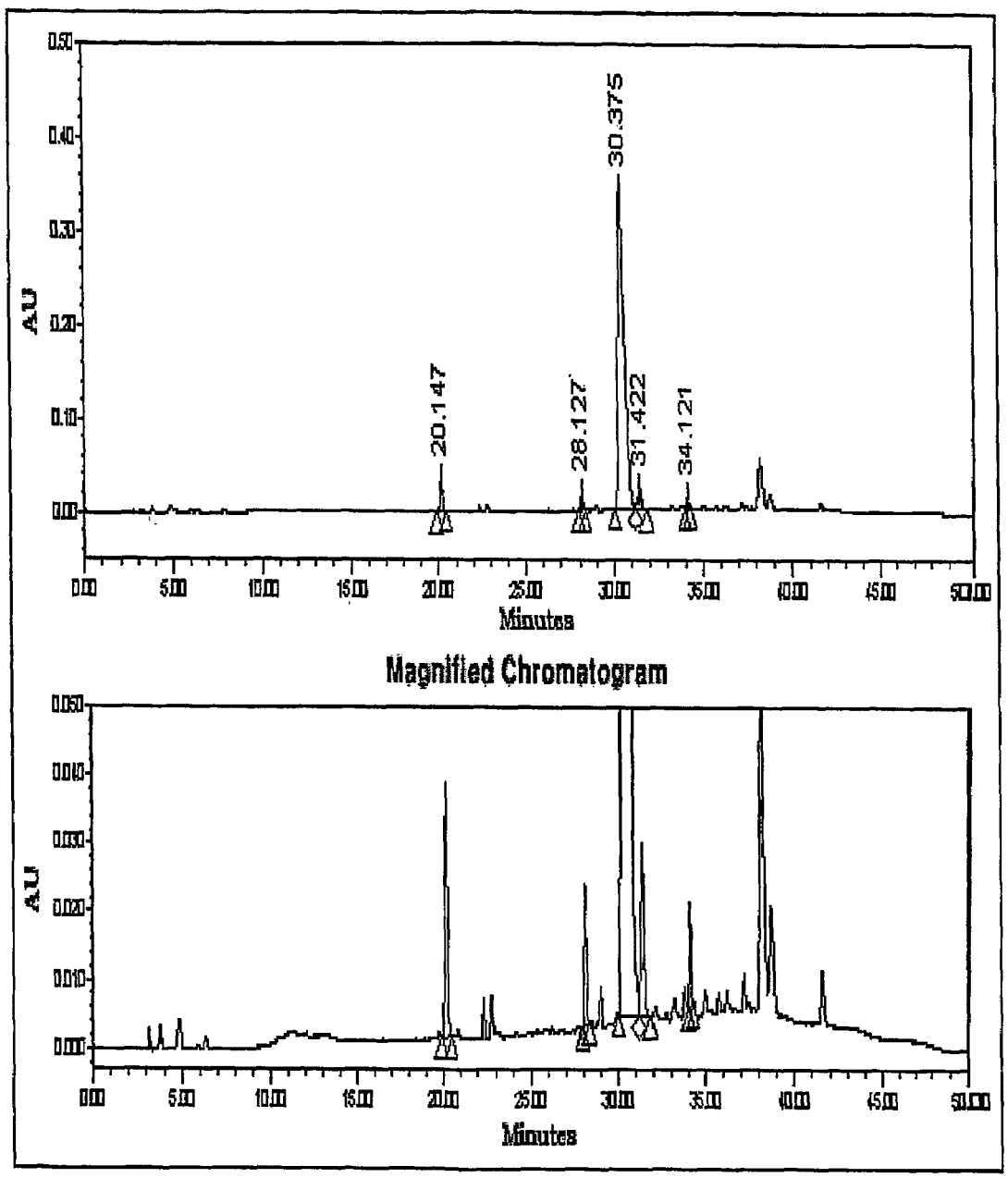

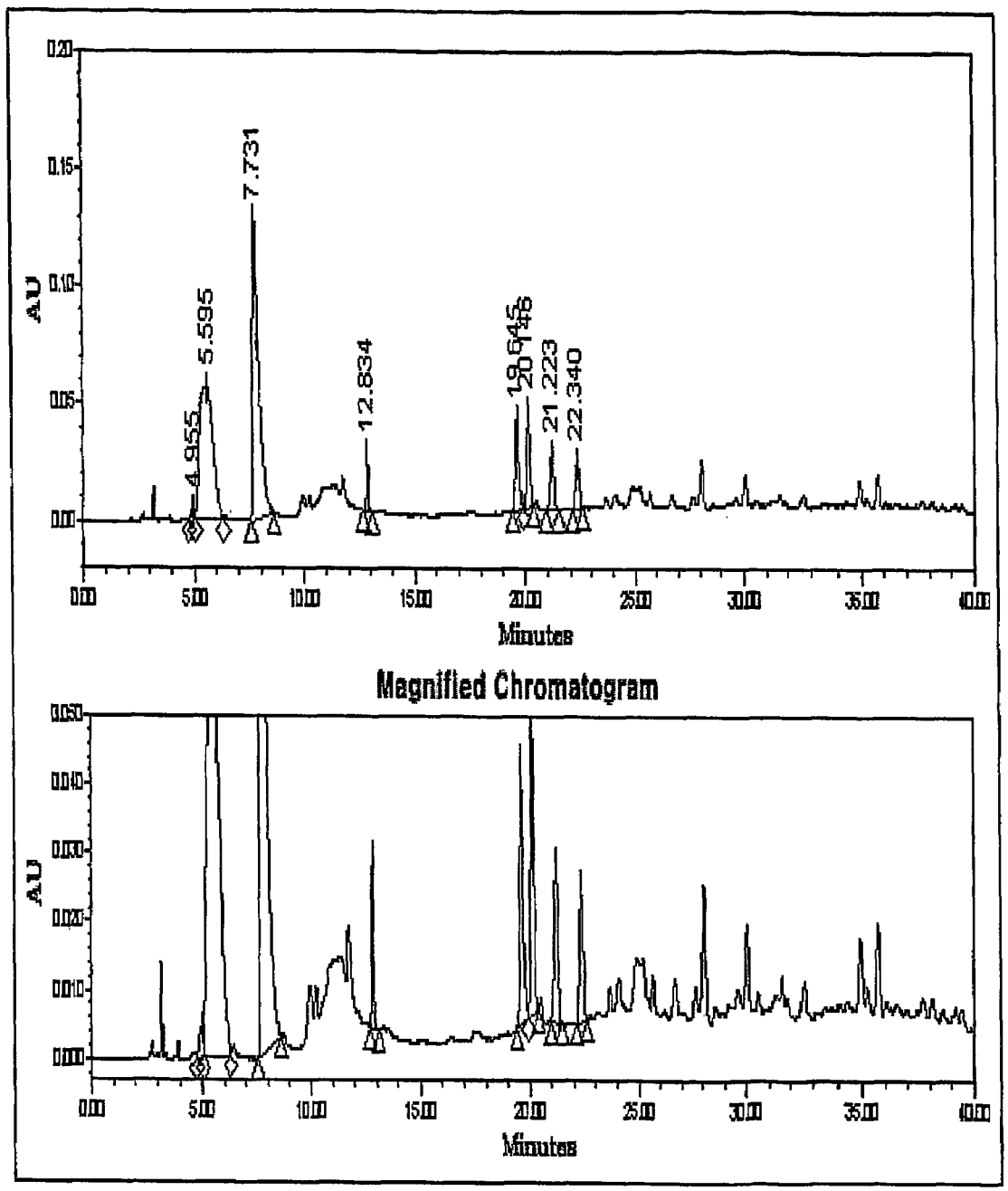
[Fig. 6]

PROCESS FOR PREPARATION OF IMIPENEM

TECHNICAL FIELD

The present invention relates to a compound of Formula II below:

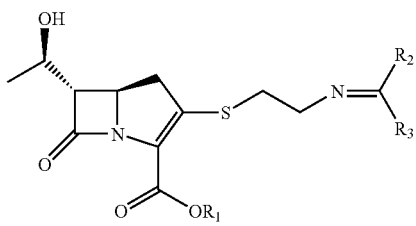

Formula II wherein $R_1$ is a p-nitrobenzyl or p-methoxybenzyl group; and $R_2$ and $R_3$ may be identical to or different from each other and are each independently a $C_{1\sim6}$ alkyl or aryl group, or a derivative thereof, and a process for preparing the compound of Formula II.

The present invention also relates to a process for preparing imipenem of Formula I below:

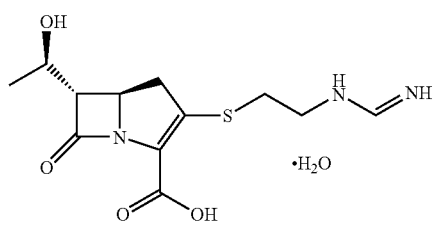

Formula I by using the compound of Formula II.

The imipenem of Formula I is a carbapenem antibiotic as a member of beta-lactam antibiotics.

BACKGROUND ART

The first carbapenem antibiotic to be discovered was thienamycin, isolated from naturally occurring *streptomyces cattleya* by Merck Co., U.S.A. in 1976.

Since thienamycin is highly chemically unstable despite superior pharmacological effects, it has not been developed into medicines. Many attempts have been made to overcome the chemical instability of thienamycin while maintaining the pharmacological effects of thienamycin. For example, imipenem, which is a novel thienamycin derivative synthesized by Merck Co., is prepared by modifying the amine group of thienamycin into an N-formimidoyl group. Imipenem is a new concept antibiotic with ensured stability. Imipenem has been widely used as a therapeutic agent to date. Imipenem as a carbapenem antibiotic is the first available compound among new type beta-lactam antibiotics possessing a carbapenem ring system, and shows high stability even in the presence of beta-lactamase. In addition, imipenem exhibits an extremely broad spectrum of antibiotic activity against gram-positive and gram-negative aerobic and anaerobic species.

Imipenem is prepared only by chemical total synthetic, unlike conventional cephalosporin antibiotics.

The first industrial synthetic of imipenem was reported in 1981. Since 1989, improved synthetic processes of imipenem have been suggested.

U.S. Pat. No. 4,292,436 discloses a process for preparing in-situ imipenem monohydrate by activating a bicyclic keto ester, reacting the activated ester with an amine-protected N-formimidoyl-2-aminoethanethiol compound, followed by catalytic hydrogenation using platinum oxide as a catalyst to remove the 2-carboxyl and the amine protecting groups without isolation of any intermediate, as depicted in Reaction Scheme 1 below:

Reaction Scheme 1

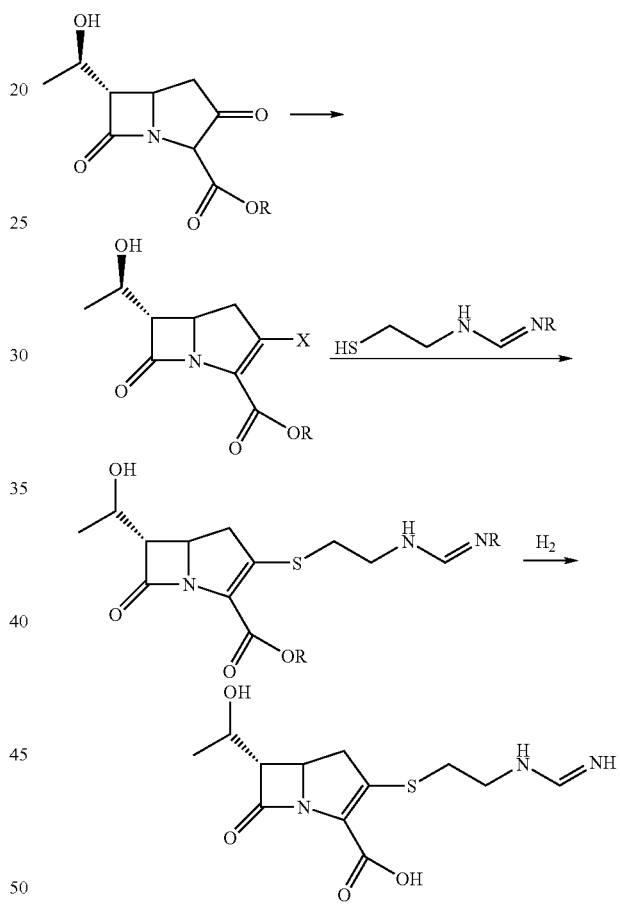

wherein R is hydrogen or a protecting group; and X is a leaving group.

However, this process has the disadvantages that the imipenem is prepared from the bicyclic keto ester in a yield as low as 35% and the process further involves four stages in the preparation of the protected N-formimidoyl 2-aminoethanethiol compound. In addition, another disadvantage of the process is that large excesses of water (660-fold amount of the starting material) and solvents are necessary for extraction upon washing after the N-formimidoyl 2-aminoethanethiol compound is introduced, resulting in an economical disadvantage.

On the other hand, U.S. Pat. Nos. 4,845,261 and 4,894,450 disclose a novel process for continuously preparing imipenem from a bicyclic keto ester via four stages without isolation and purification of any intermediates. The procedure of the process is depicted in Reaction Scheme 2 below:

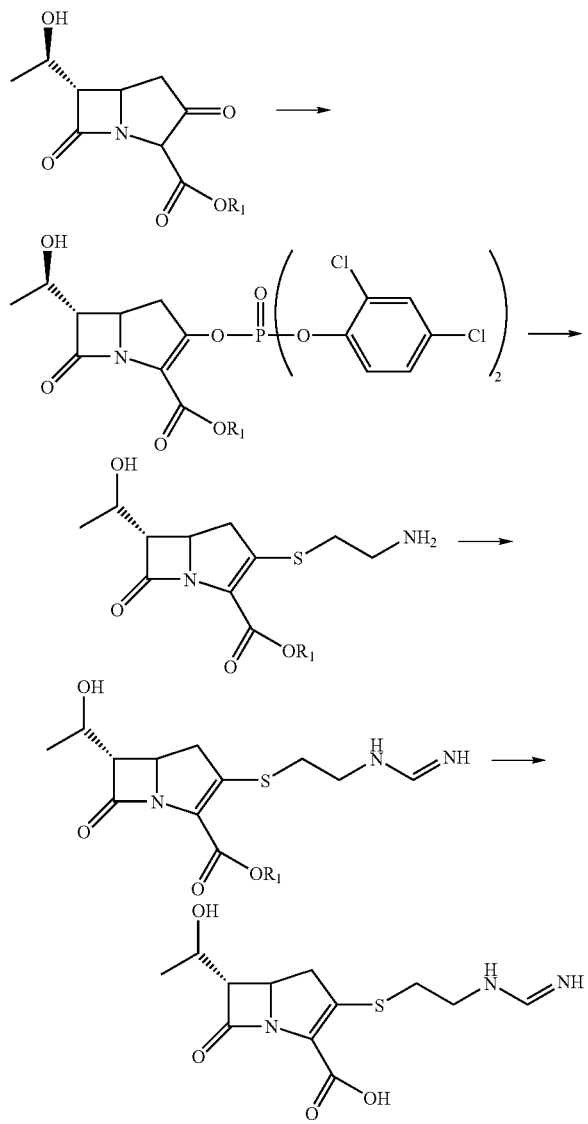

wherein R, is a p-nitrobenzyl group.

As depicted in Reaction Scheme 1, since the process consisting of four stages proceeds in-situ without undergoing any separation and purification, the final product inevitably contains large amounts of impurities, which makes the separation and purification of the final product difficult. In addition, the process is accompanied by the use of costly bis(dichlorophenyl)phosphorochloridate in order to activate the bicyclic keto ester precursor.

Since expensive N-ethylpyrrolidinone used as a reaction solvent in Reaction Scheme 2 is a highly polar organic solvent, it is difficult to remove the solvent from the resulting aqueous solution after completion of the reaction. Further, the excessive use of the reaction solvent (200-fold amount of the starting material) creates an economic burden in the industrialization of the process.

U.S. Pat. No. 4,373,772 proposes a semi-synthetic process of imipenem monohydrate using thienamycin isolated from *streptomyces cattleya* as a starting material. The overall procedure of this process is depicted in Reaction Scheme 3 below:

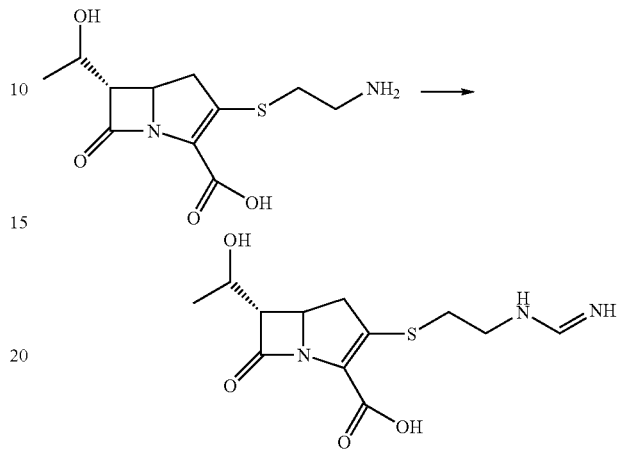

As depicted in Reaction Scheme 3, however, since the chemically unstable thienamycin is obtained in a small amount from the microorganism, the process is disadvantageous in terms of poor economic efficiency. In addition, the use of an excess of water (214-fold amount of the starting material) as a reaction solvent causes difficulties in reaction, separation, and purification. Furthermore, the process has the disadvantage that 5% or more of dimer bis-thienamycin formamidine is formed as an undesired reaction by-product along with the desired product imipenem.

Dr. Ranbaxy filed an international PCT application (WO 02/36594) relating to a process for preparing imipenem. This process is similar to the process of Merck Co., except that a mixed solvent of tetrahydrofuran and costly 1,3-dimethyl-3,4,5,6-tetrahydro-(2H)-pyrimidinone is used as a reaction solvent. However, the publication does not refer to a hydrogenation catalyst. In addition, the final product imipenem in a crystalline form is prepared in a very low yield of 23% from a bicyclic keto ester as a starting material by adsorption chromatography.

DISCLOSURE OF THE INVENTION

As stated above, according to the conventional processes for preparing imipenem, since the intermediates are impossible to separate and purify or are unstable, the product imipenem is prepared via continuous reaction stages (in-situ reaction). As a result, the formation of large amounts of impurities is inevitable.

For these reasons, the large amounts of impurities cause difficulties in work-up, separation and purification, leading to low yield and purity of the final product.

In other words, according to the conventional synthetic processes of imipenem, since the overall reaction stages continuously proceed without any separation of the intermediates due to poor chemical stability of the intermediates, the isolation and purification of imipenem are performed in the presence of impurities. In addition, the isolation by crystallization is difficult due to the presence of impurities, resulting in low yield and purity of the final product.

Furthermore, since the conventional processes require the use of expensive reaction solvents and large excesses of solvents (200-fold amounts of the starting materials), they have problems in terms of poor economic efficiency and industrial application.

Therefore, the present invention has been made in view of the above problems, and it is an object of the present invention to provide the novel amine-protected thienamycin compound of Formula II useful in the preparation of imipenem monohydrate of Formula I, and a process for preparing the thienamycin compound of Formula II.

It is another object of the present invention to provide a process for preparing imipenem using the amine-protected thienamycin compound of Formula II.

As explained above, according to the compound of Formula II or a derivative thereof of the present invention, different protecting groups are effectively introduced into the carboxyl group and amine group of thienamycin to obtain the amine-protected thienamycin compound of Formula II as a imipenem intermediate, which is used in the preparation of the imipenem monohydrate of Formula I. According to the process of the present invention, the problem of low yield of imipenem monohydrate due to the presence of large amounts of impurities, resulting from no isolation and purification of intermediates, can be solved. In addition, the imipenem monohydrate with a high purity can be prepared from the novel intermediate compound of Formula II in a simple manner. Furthermore, the yield and quality of the imipenem monohydrate of Formula I can be greatly improved.

Since the process of the present invention uses common organic solvents and water, the solvents are readily removed after completion of the reaction. In addition, since a palladium catalyst containing a large amount of water is used in the hydrogenation for the removal of the protecting groups, the danger upon handling is considerably reduced, allowing the process of the present invention to proceed under mild reaction conditions. Accordingly, the process of the present invention is economically advantageous and enables the preparation of imipenem with no difficulty.

BRIEF DESCRIPTION OF THE DRAWINGS

The above and other objects, features and other advantages of the present invention will be more clearly understood from the following detailed description taken in conjunction with the accompanying drawings, in which:

FIG. 1 is an LC chromatogram showing the purity of a ketone compound;

FIG. 2 is an LC chromatogram showing the purity of an imine compound;

FIG. 3 is an LC chromatogram showing Merck-formimidation;

FIG. 4 is an LC chromatogram showing Merck-hydrogenation;

FIG. 5 is an LC chromatogram showing CWP (Choongwae Pharma Corp.)-formimidation; and FIG. 6 is an LC cromatogram showing CWP-hydrogenation.

BEST MODE FOR CARRYING OUT THE INVENTION

EXAMPLE 1

Preparation of (5R,6S)p-nitrobenzyl-3-(diphenylphosphono)-6-[(1R)-1-hydroxyethyl]-1-azabicyclo[3.2.0]hept-2-ene-7-one-2-carboxylate 20.0 g of (5R,6S)p-nitrobenzyl-6-[(1R)-1-hydroxyethyl]-1-azabicyclo[3.2.0]hept-3,7-dione-2-carboxylate of Formula III below was dissolved in a mixture solution of acetonitrile (100 ml), and tetrahydrofuran (100 ml). The reaction temperature was lowered to 0° C.~−10° C. To the reaction mixture were sequentially added 11.1 g of N,N-diisopropylethylamine and 18.5 g of diphenylchlorophosphate. The resulting mixture was stirred for 1.5~2 hours while maintaining the reaction temperature at −10° C., giving the enol phosphate of Formula IV below. The enol phosphate of Formula IV was used in the next step without further separation.

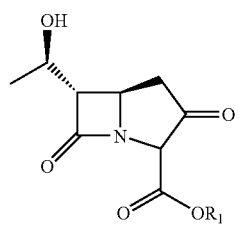

Formula III wherein $R_1$ is p-nitrobenzyl.

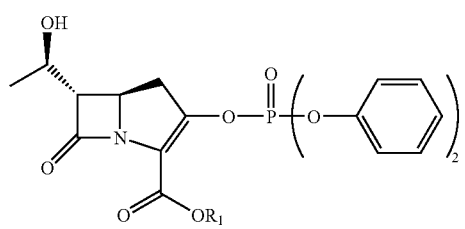

Formula IV wherein $R_1$ is p-nitrobenzyl.

EXAMPLE 2

Preparation of (5R,6S)p-nitrobenzyl 6-[(1R)-1-hydroxyethyl]-3-({2-[(1-isopropylidene)amino]ethyl}thio)-1-azabicyclo[3.2.0]hept-2-ene-7-one-2-carboxylate A reaction solution of the enol phosphate derivative of Formula IV prepared in Example 1 was lowered from −40° C. to −60° C., and then 7.8 g of 2-aminoethanethiol hydrochloride and 11.1 g of diisopropylamine were sequentially added thereto. The reaction mixture was stirred for 0.5~1 hour at the same temperature. A ketone type solvent was added to the reaction mixture in the presence of a base, stirred, and crystallized. The obtained precipitate was filtered, washed with hexane, and dried under reduced pressure at room temperature, affording 20.5 g (yield: 80.0%) of the amine-protected thienamycin of Formula II.

$^1$H-NMR (DMSO-$d_6$, 300 MHz, ppm) δ 1.14 (d, J=6.3 Hz, 3H), 1.78 (s, 3H), 1.90 (s, 3H), 3.12 (m, 2H), 3.28-3.32 (m, 2H), 3.37-3.40 (m, 2H), 3.94 (m, 1H), 4.13 (dt, J=2.4, 8.7 Hz, 1H), 5.07 (d, J=5.1 Hz, 1H), 5.27 (d, J=14.1 Hz, 1H), 5.43 (d, J=14.1 Hz, 1H), 7.70 (d, J=8.7 Hz, 2H), 8.22 (d, J=8.7 Hz, 2H)

Mass: 447.51

M.p.: 148~151° C.

Color: Pale yellow.

EXAMPLE 3

Preparation of (5R,6S)p-nitrobenzyl-3-[[2-[(formimidoylamino)ethyl]thio]-6-[(1 R)-1-hydroxyethyl]-1-azabicyclo[3.2.0]hept-2-ene-7-one-2-carboxylate After 20.0 g of the intermediate compound of Formula II prepared in Example 2 was added to a mixed solvent of distilled water and tetrahydrofuran, the reaction temperature was lowered from 5° C. to −5° C. or lower. To there action mixture were added 18 ml of N-methylmorpholine and 30.8 g of benzylformimidate hydrochloride. The resulting mixture was stirred at 0~10° C. for 2~3 hours, affording the compound of Formula V, which was used in the next step without further separation.

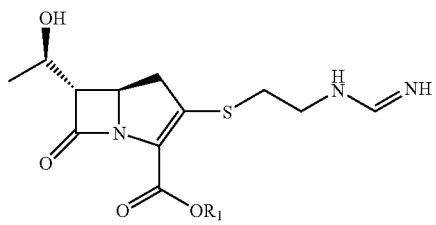

Formula V wherein $R_1$ is p-nitrobenzyl.

EXAMPLE 4

Preparation of (+)-(5R,6S)-3-{[2-(formimidoylamino)ethyl]thio}-6-[(R)-1-hydroxyethyl]-7-oxo-1-azabicyclo[3.2.0]hept-2-ene-2-carboxylic acid(imipenem)

To a reaction solution of the carboxyl-protected N-formimidoyl thienamycin of Formula V prepared in Example 3, 16 g of N-methylmorpholine was added to adjust the pH to 7.0~8.0. A water-containing palladium catalyst was added to the reaction mixture to proceed a deprotection reaction at 10~25° C. At this time, the reaction was continued for 3 hours while maintaining the hydrogen pressure at 4~6 kg/cm$^2$, and then the catalyst was removed by filtration. HPLC analysis of the reaction solution indicated that imipenem was prepared in a yield of 82%. The reaction solution was washed several times with ethyl acetate, and evaporated under reduced pressure to remove residual organic solvents. The resulting aqueous solution was purified by reversed-phase column chromatography, followed by concentration using a reverse osmosis technique. Acetone was added to the concentrate, stirred for 2~3 hours, and crystallized. The crystallized imipenem monohydrate was filtered, washed, and dried under reduced pressure, affording 8.6 g of the desired imipenem monohydrate of Formula I (yield: 60%, purity (by HPLC): 99%).

Hereinafter, the preparation process of imipenem according to the present invention (hereinafter, referred to as "the present process") was compared with that of Merck. Co. (see, U.S. Pat. Nos. 4,845,261 and 4,894,450, hereinafter referred to as "Merck's process").

<Experiments>

According to Merck's process, imipenem was prepared without separation of any intermediates. In contrast, according to the present process, the imine compound was prepared from the carboxyl-protected thienamycin, separated, and used to prepare imipenem. Thereafter, the yield and content of imipenem were compared.

<Experimental procedures>

In the case of Merck's process, imipenem was prepared in accordance with the procedure described in U.S. Pat. Nos. 4,845,261 and 4,894,450, except that bis(dichlorophenyl) phosphorochloridate sold by TCI was used.

<Results>

In order to compare the experimental results of the present process with those of Merck's process, the following samples were used:
   Ketone compound (Formula III)
   Imine compound (Formula II)
   Merck's process: Formimidation & imipenem
   The process of the present invention: Formimidation & imipenem Apparatuses and conditions for LC analysis employed for comparing the experimental results of the present process with those of Merck's process, were as follows:
   1) Analytical apparatus
   Alliance 2695 & 2996 PDA system
   Workstation: Empower
   Column: C18, ODS, 4.6×260 mm, 5 μm
   2) Analytical conditions
   i) HPLC
   Flow rate: 1.0 mL/min.
   Injection Volume: 5 μl
   Sampling: 1/10 dilutions (by mobile phase B)
   Run time: 50 min.
   Column temperature: Room temperature
   Auto sampler temperature: 4° C.
   Detector: 254 nm
   ii) Mobile phases
   Mobile phase A: $(NH_4)_2HPO_4$ buffer
   Mobile phase B: MeOH/ACN=1:1
   The gradient conditions of the mobile phases are shown in Table 1 below:

TABLE 1

|  | 0 (min.) | 5 (min.) | 35 (min.) | 40 (min.) | 45 (min.) | 50 (min.) |
| --- | --- | --- | --- | --- | --- | --- |
| Mobile phase A | 95 | 95 | 20 | 20 | 95 | 95 |
| Mobile phase B | 5 | 5 | 80 | 80 | 5 | 5 |

<Experimental Results>

1) Purity of ketone-Compound

The ketone compound is a reaction compound used in both Merck's process and the present process. The ketone compound prepared in the present process was used in Merck's process. The purity of the ketone compound is shown in Table 2 below.

TABLE 2

| Purity of ketone compound | |
| --- | --- |
| Unknown (%) | Main (%) |
| 13.2 | 86.2 |

An LC chromatogram showing the purity of the ketone compound is shown in FIG. 1.

2) Purity of Imine Compound:

The imine compound separated in accordance with the present process is a compound distinguishing the present process from Merck's process, and is a key compound for the present experimental purpose. Table 3 shows the purity of the imine compound.

TABLE 3

| Purity of imine compound |
|---|
| 96.3 (%) |

An LC chromatogram showing the purity of the imine compound is shown in FIG. 1.

3) Comparison of Purities Based on the Respective Steps of Merck's Process and the Present Process Table 4 shows the purities of the respective steps in both processes.

TABLE 4

|  | Ketone | Imine | Formimidation |
|---|---|---|---|
| Merck's process | 86.2% | — | 72.1% |
| The present process | 86.2% | 96.3% | 87.5% |

4) Comparison of Yields Based on the Respective Steps of Merck's Process and the Present Process (Relative to Theoretical Values)

Table 5 shows the yields of the respective steps in both processes.

TABLE 5

|  |  | Ketone | Imine | Imipenem |
|---|---|---|---|---|
| Merck's process | Content |  |  | 0.363 g |
|  | Theoretical content |  |  | 0.851 g |
|  | Yield (Relative to the theoretical value) |  |  | 42.3% |
| The present process | Content |  | 2.4 g | 1.221 g |
|  | Theoretical content |  | 3.2 g | 1.672 g |
|  | Yield (Relative to the theoretical value) |  | 75.0% | 73.3% |

Since Merck's process does not include the step of preparing the imine compound, the imine compound content could not be calculated. The theoretical contents based on the respective steps indicate contents obtained when the corresponding yields were 100%.

The imipenem content was calculated based on the content of imipenem anhydride. Water content and other factors were excluded from the calibration (since the state was liquid, the factor values could not be exactly calculated).

The imipenem content was obtained by comparing the calculated peak area with the peak area of the USP standard reagent.

FIGS. 3 through 6 are LC chromatograms showing Merck-formimidation, Merck-hydrogenation, CWP-formimidation, and CWP-hydrogenation, respectively.

As is evident from the above experimental results, the present process wherein the imine compound was separated to prepare imipenem, was superior to Merck's process in the contents of the compound obtained after the formimidation and the final product imipenem.

In accordance with one aspect of the present invention, the above objects can be accomplished by a compound of Formula II below:

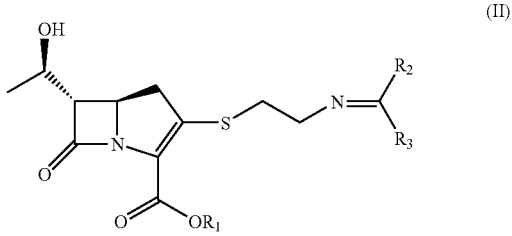

(II)

wherein $R_1$ is a p-nitrobenzyl or p-methoxybenzyl group; and $R_2$ and $R_3$ may be identical to or different from each other and are each independently a $C_{1~6}$ alkyl or aryl group, or a derivative thereof.

In accordance with another aspect of the present invention, there is provided a process for preparing the compound of Formula II by coupling a compound of Formula IV below:

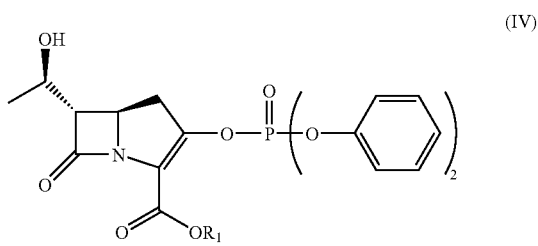

(IV)

wherein $R_1$ is a p-nitrobenzyl or p-methoxybenzyl group, or a derivative thereof with 2-aminoethanethiol hydrochloride in the presence of a base, followed by reaction with a ketone.

The ketone is selected from the group consisting of acetone, methylethylketone, diphenylketone, and mixtures thereof.

The compound of Formula IV or a derivative thereof is obtained by condensing a compound of Formula III below:

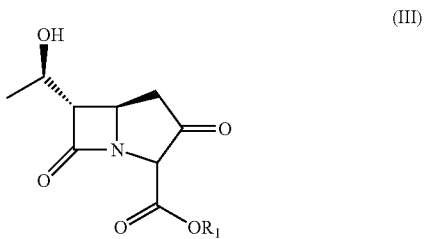

(III)

wherein $R_1$ is a p-nitrobenzyl or p-methoxybenzyl group, with diphenylchlorophosphate in the presence of a base.

As the reaction solvent, a mixed solvent of acetonitrile and tetrahydrofuran is used.

The reaction temperature is within the range of 0° C. to −10° C.

In accordance with yet another aspect of the present invention, there is provided a process for preparing the compound of Formula I below:

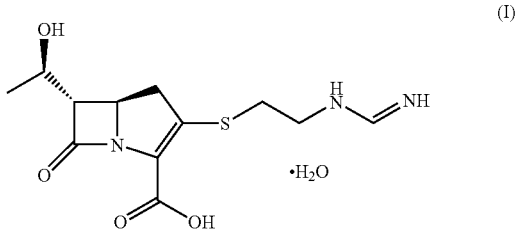

(I)

by reacting the compound of Formula II with isopropylformimidate or benzylformimidate in the presence of a base to obtain a compound of Formula V below:

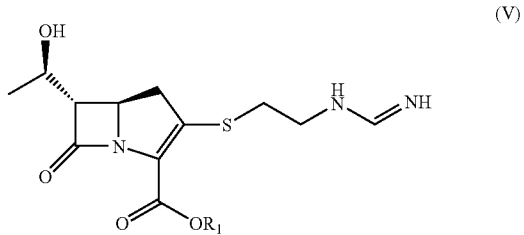

(V)

wherein $R_1$ is a p-nitrobenzyl or p-methoxybenzyl group, hydrogenating the compound of Formula V in the presence of a metal catalyst, separating the hydrogenated compound, and crystallizing the separated compound in the presence of an alcohol or ketone.

The hydrogenation is carried out in the presence of a palladium catalyst containing an excess of water under a hydrogen pressure of 4~6 kg/cm².

As a solvent for the reaction, a mixed solvent of water and tetrahydrofuran is used.

The present invention will now be described in more detail.

According to the present invention, the amine-protected thienamycin compound of Formula II is prepared by coupling the enol phosphate derivative of Formula IV with 2-aminoethanethiol hydrochloride, followed by reaction with an appropriate ketone. The amine-protected thienamycin compound thus prepared is useful in the preparation of the imipenem monohydrate of Formula I.

According to the present invention, different protecting groups are effectively introduced into the carboxyl and amine groups of the thienamycin derivative used in conventional preparation processes of imipenem to prepare the amine-protected thienamycin compound of Formula II as a carbapenem intermediate. The amine-protected thienamycin compound thus prepared is stable at room temperature and can be stored at low temperature for a long period of time.

That is, according to the present invention, the bicyclic keto ester of Formula III is condensed with diphenylchlorophosphate in the presence of a base to prepare the enol phosphate compound of Formula IV.

The enol phosphate derivative of Formula IV is prepared in a polar solvent selected from ethers, e.g., tetrahydrofuran, diisopropyl ether and dioxane and acetonitrile, and then the enol phosphate derivative is coupled with 2-aminoethanethiol hydrochloride in the presence of a base to prepare the thienamycin derivative. Thereafter, a common ketone, such as acetone, methylethyl ketone or diphenylketone, is added to the thienamycin derivative to prepare the amine-protected thienamycin compound of Formula II, which is then isolated and crystallized.

Unlike conventional preparation processes of imipenem, different protecting groups are effectively introduced into the carboxyl and amine groups of thienamycin to prepare the amine-protected thienamycin compound of Formula II as a carbapenem intermediate. The compound of Formula II is a novel compound in the form of a pale white crystal that is stable at room temperature and can be stored at low temperature for a long period of time. In addition, the compound of Formula II is useful as an intermediate for the preparation of an imipenem intermediate and in the preparation of other carbapenem antibiotics.

Further, according to the present invention, the amine-protected thienamycin compound as a novel intermediate is effectively used in the preparation of the imipenem monohydrate of Formula I.

Further, according to the present invention, the compound of Formula II is reacted with isopropylforimidate hydrochloride or benzylforimidate hydrochloride in the presence of a base to prepare the carboxyl group-protected imipenem of Formula V, hydrogenating the carboxyl group-protected imipenem in the presence of a metal catalyst to remove the protecting group, followed by appropriate treatment, to obtain an aqueous solution, which is then separated by reversed-phase column chromatography and crystallized in an appropriate alcohol or ketone to prepare the high-purity imipenem monohydrate of Formula I in high yield.

INDUSTRIAL APPLICABILITY

As explained above, according to the compound of Formula II or a derivative thereof of the present invention, different protecting groups are effectively introduced into the carboxyl group and amine group of thienamycin to obtain the amine-protected thienamycin compound of Formula II as a imipenem intermediate, which is used in the preparation of the imipenem monohydrate of Formula I. According to the process of the present invention, the problem of low yield of imipenem monohydrate due to the presence of large amounts of impurities, resulting from no isolation and purification of intermediates, can be solved. In addition, the imipenem monohydrate with a high purity can be prepared from the novel intermediate compound of Formula II in a simple manner. Furthermore, the yield and quality of the imipenem monohydrate of Formula I can be greatly improved.

Since the process of the present invention uses common organic solvents and water, the solvents are readily removed after completion of the reaction. In addition, since a palladium catalyst containing a large amount of water is used in the hydrogenation for the removal of the protecting groups, the danger upon handling is considerably reduced, allowing the process of the present invention to proceed under mild reaction conditions. Accordingly, the process of the present invention is economically advantageous and enables the preparation of imipenem with no difficulty.

What is claimed is:

1. A compound of Formula II below:

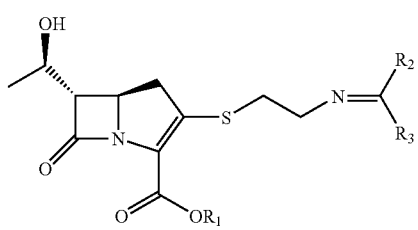

wherein

R₁ is a p-nitrobenzyl or p-methoxybenzyl group; and R₂ and R₃ may be identical to or different from each other and are each independently a $C_{1\sim6}$ alkyl or aryl group.

2. A process for preparing a compound of Formula II below:

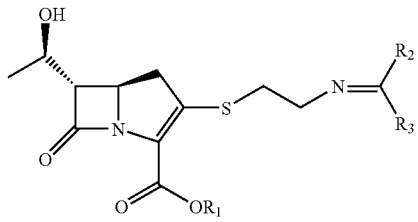

wherein

R₁ is a p-nitrobenzyl or p-methoxybenzyl group; and R₂ and R₃ may be identical to or different from each other and are each independently a $C_{1\sim6}$ alkyl or aryl group, by coupling a compound of Formula IV below:

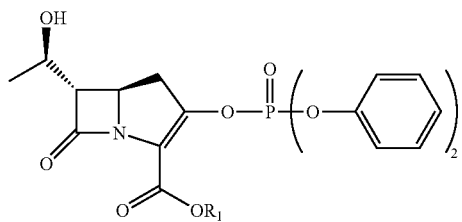

wherein R₁ is a p-nitrobenzyl or p-methoxybenzyl group, with 2-aminoethanethiol hydrochloride in the presence of a base, followed by reaction with a ketone.

3. The process according to claim 2, wherein the ketone is selected from the group consisting of acetone, methylethylketone, diphenylketone, and mixtures thereof.

4. The process according to claim 2 or 3, wherein the compound of Formula IV is obtained by condensing a compound of Formula III below:

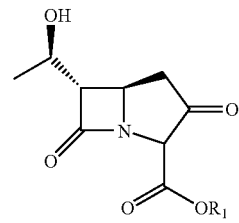

wherein

R₁ is a p-nitrobenzyl or p-methoxybenzyl group, with diphenylchlorophosphate in the presence of a base.

5. The process according to claim 4, wherein the reaction solvent is a mixed solvent of acetonitrile and tetrahydrofuran.

6. The process according to claim 4, wherein the condensation is carried out at a temperature within the range of 0° C. to −10° C.

7. A process for preparing the compound of Formula I below:

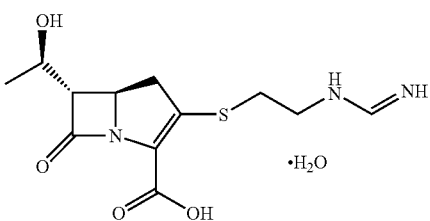

by reacting a compound of Formula II below:

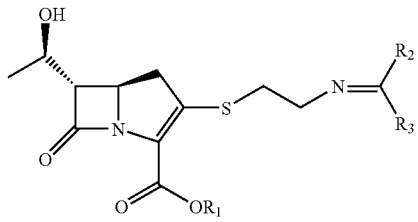

wherein

R₁ is a p-nitrobenzyl or p-methoxybenzyl group; and R₂ and R₃ may be identical to or different from each other and are each independently a $C_{1\sim6}$ alkyl or aryl group, with isopropylformimidate or benzylformimidate in the presence of a base to obtain a compound of Formula V below:

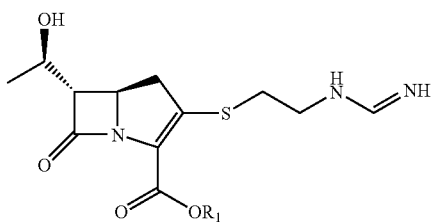

(V)

wherein

R₁ is a p-nitrobenzyl or p-methoxybenzyl group, hydrogenating the compound of Formula V in the presence of a metal catalyst, separating the hydrogenated compound, and crystallizing the separated compound in the presence of an alcohol or ketone.

8. The process according to claim 7, wherein the hydrogenation is carried out in the presence of a palladium catalyst containing an excess of water under a hydrogen pressure of 4~6 kg/cm².

9. The process according to claim 7, wherein the reaction solvent is a mixed solvent of water and tetrahydrofuran.

* * * * *